(12) United States Patent
Fortin et al.

(10) Patent No.: US 8,343,062 B2
(45) Date of Patent: Jan. 1, 2013

(54) DIGITAL CONTROL METHOD FOR MEASURING BLOOD PRESSURE

(75) Inventors: Jürgen Fortin, Graz (AT); Rupert Grüllenberger, Graz (AT)

(73) Assignee: CNSystems Medizintechnik AG, Graz (AT)

( * ) Notice: Subject to any disclaimer, the term of this patent is extended or adjusted under 35 U.S.C. 154(b) by 0 days.

(21) Appl. No.: 12/915,572

(22) Filed: Oct. 29, 2010

(65) Prior Publication Data

US 2011/0105917 A1 May 5, 2011

Related U.S. Application Data

(60) Provisional application No. 61/256,081, filed on Oct. 29, 2009, provisional application No. 61/256,110, filed on Oct. 29, 2009.

(51) Int. Cl.
*A61B 5/02* (2006.01)

(52) U.S. Cl. ........ 600/485; 600/490; 600/500; 600/483; 600/479

(58) Field of Classification Search .......... 600/473–481, 600/483, 484, 500–504
See application file for complete search history.

(56) References Cited

U.S. PATENT DOCUMENTS

| | | |
|---|---|---|
| 4,406,289 A | 9/1983 | Wesseling et al. |
| 4,510,940 A | 4/1985 | Wesseling |
| 4,524,777 A | 6/1985 | Kisioka et al. |
| 4,539,997 A | 9/1985 | Wesseling et al. |
| 4,592,364 A | 6/1986 | Pinto |
| 4,705,047 A | 11/1987 | Bailey |
| 4,726,382 A | 2/1988 | Boehmer et al. |
| 4,869,261 A | 9/1989 | Penaz |
| 4,899,758 A | 2/1990 | Finkelstein et al. |
| 5,054,493 A | 10/1991 | Cohn et al. |
| 5,172,696 A * | 12/1992 | Souma .......................... 600/473 |
| 5,211,177 A | 5/1993 | Chesney et al. |
| 5,265,011 A | 11/1993 | O'Rourke |
| 5,400,793 A | 3/1995 | Wesseling |
| 5,485,838 A * | 1/1996 | Ukawa et al. .................. 600/330 |
| 5,533,511 A | 7/1996 | Kaspari et al. |
| 5,535,753 A | 7/1996 | Petrucelli et al. |
| 5,575,284 A | 11/1996 | Athan et al. |
| 5,676,140 A * | 10/1997 | Ukawa et al. .................. 600/311 |
| 5,746,698 A | 5/1998 | Bos et al. |

(Continued)

FOREIGN PATENT DOCUMENTS

AT 407949 7/2001

(Continued)

OTHER PUBLICATIONS

Peñáz J: Photoelectric Measurement of blood pressure, volume and flow in the finger. Digest of the 10th international conference on medical and biological engineering—Dresden (1973).

*Primary Examiner* — Navin Natnithithadha
(74) *Attorney, Agent, or Firm* — McDonnell Boehnen; Hulbert Berghoff LLP

(57) ABSTRACT

A system and method of digital control for a blood pressure measurement system is provided. According to at least one embodiment, a photo-plethysmographic (PPG) system produces a frequency signal that corresponds to the measured light in the PPG system. Such light may be indicative of blood volume in a vein or artery. The frequency signal may be used to control one or more pressure valves of the system in order to measure blood pressure and hold the frequency signal constant.

18 Claims, 6 Drawing Sheets

U.S. PATENT DOCUMENTS

| | | | | |
|---|---|---|---|---|
| 6,011,985 | A | 1/2000 | Athan et al. | |
| 6,315,735 | B1 | 11/2001 | Joeken et al. | |
| 6,348,038 | B1 | 2/2002 | Band et al. | |
| 6,394,958 | B1 | 5/2002 | Bratteli et al. | |
| 6,471,646 | B1 | 10/2002 | Thede | |
| 6,496,711 | B1 | 12/2002 | Athan et al. | |
| 6,623,434 | B2 | 9/2003 | Chesney et al. | |
| 6,669,648 | B1 * | 12/2003 | Fortin et al. | 600/490 |
| 6,689,069 | B2 | 2/2004 | Bratteli et al. | |
| 6,733,461 | B2 | 5/2004 | Bratteli | |
| 6,736,782 | B2 | 5/2004 | Pfeiffer et al. | |
| 6,758,822 | B2 | 7/2004 | Romano | |
| 7,035,679 | B2 | 4/2006 | Addison et al. | |
| 7,144,372 | B2 | 12/2006 | Ng et al. | |
| 7,220,230 | B2 | 5/2007 | Roteliuk et al. | |
| 7,317,409 | B2 | 1/2008 | Conero | |
| 7,318,807 | B2 | 1/2008 | Ng | |
| 7,361,147 | B2 | 4/2008 | Ng | |
| 7,390,301 | B2 | 6/2008 | Skrabal et al. | |
| 7,422,562 | B2 | 9/2008 | Hatib et al. | |
| 7,442,169 | B2 | 10/2008 | O'Rourke | |
| 7,452,333 | B2 | 11/2008 | Roteliuk | |
| 7,503,897 | B2 | 3/2009 | Ng et al. | |
| 7,588,542 | B2 | 9/2009 | Pfeiffer et al. | |
| 7,628,758 | B2 | 12/2009 | O'Rourke | |
| 7,651,466 | B2 | 1/2010 | Hatib et al. | |
| 7,666,144 | B2 | 2/2010 | Cohen et al. | |
| 7,803,122 | B2 | 9/2010 | Pfeiffer et al. | |
| 7,815,578 | B2 | 10/2010 | Cohen et al. | |
| 2005/0124904 | A1 | 6/2005 | Roteliuk | |
| 2005/0228298 | A1 * | 10/2005 | Banet et al. | 600/485 |
| 2006/0235323 | A1 | 10/2006 | Hatib et al. | |
| 2007/0032729 | A1 | 2/2007 | Fortin | |
| 2008/0015451 | A1 | 1/2008 | Hatib et al. | |
| 2008/0200785 | A1 | 8/2008 | Fortin | |
| 2008/0287812 | A1 | 11/2008 | Parlikar et al. | |
| 2009/0062666 | A1 | 3/2009 | Roteliuk | |
| 2009/0112113 | A1 | 4/2009 | Mukkamala | |
| 2009/0270739 | A1 | 10/2009 | Hatib et al. | |
| 2010/0016735 | A1 | 1/2010 | Harpas et al. | |
| 2010/0076326 | A1 | 3/2010 | Cohen et al. | |
| 2010/0121203 | A1 | 5/2010 | O'Rourke et al. | |
| 2010/0198088 | A1 | 8/2010 | Ortenberg et al. | |
| 2010/0204592 | A1 | 8/2010 | Hatib et al. | |
| 2010/0217134 | A1 | 8/2010 | Van Goudoever et al. | |
| 2010/0241013 | A1 | 9/2010 | Hatib | |

FOREIGN PATENT DOCUMENTS

| | | |
|---|---|---|
| EP | 0537383 | 4/1993 |
| EP | 1103217 | 5/2001 |
| WO | 96/26497 | 8/1996 |
| WO | 96/29004 | 9/1996 |
| WO | 97/15230 | 5/1997 |
| WO | 97/24982 | 7/1997 |
| WO | 99/02086 | 1/1999 |
| WO | 99/48023 | 9/1999 |
| WO | 2004/075746 | 9/2004 |
| WO | 2005/037097 | 4/2005 |
| WO | 2005/055825 | 6/2005 |
| WO | 2005/084536 | 9/2005 |
| WO | 2007/062456 | 7/2007 |
| WO | 2009/101140 | 8/2009 |
| WO | 2010/091055 | 8/2010 |

* cited by examiner

US 8,343,062 B2

DIGITAL CONTROL METHOD FOR MEASURING BLOOD PRESSURE

CROSS REFERENCE TO RELATED APPLICATIONS

The present application is a non-provisional of U.S. provisional patent application Ser. No. 61/256,081 filed Oct. 29, 2009, the entire contents of which are incorporated herein by reference.

The present application is also a non-provisional of U.S. provisional patent application Ser. No. 61/256,110 filed Oct. 29, 2009, the entire contents of which are incorporated herein by reference.

BACKGROUND

1. Field

The invention relates generally to a method of measuring blood pressure, and more particularly to a method of reducing the effects of noise in the light signal of a PPG blood pressure measuring system.

2. Description of Related Art

Pulse contour analysis (PCA) is the process of calculating parameters from a blood pressure pulse, especially from the contour of the pulse wave. PCA begins with measuring blood pressure (BP).

Blood pressure may be measured in a number of ways. As one example, a standard non-invasive sphygmomanometer (NBP) may be placed on the upper arm or wrist. The NBP applies pressure to the arteries, causing them to constrict and limit blood flow. As the pressure is released, blood flow is restored in the artery, and the systolic and diastolic blood pressures may be measured. NBP measures BP intermittently and not continuously, so it cannot be used for PCA.

Another device for measuring blood pressure is a finger cuff having an infrared light source and a light detector for measuring a photo-plethysmographic (PPG) signal that is known also from pulsoximetry. This PPG-signal is fed into a control system, which produces a counter pressure in the finger cuff. The counter pressure equals intra-arterial pressure when the PPG-signal is kept constant. Thus, the counter pressure, which is indirectly equivalent to intra-arterial pressure, is measured. This method is known as "Vascular Unloading Technique" and the continuous pressure signal can be used for PCA.

Invasive devices may also be used to measure blood pressure, such as an intra-arterial catheter, for example. Intra-arterial transducers have relatively high frequency transmission (up to 200 Hz) and can therefore be used for PCA.

Some example parameters that may be calculated from the contour of the pulse wave include stroke volume (SV), cardiac output (CO), stroke volume variation (SVV), pulse pressure variation (PPV), and total peripheral resistance (TPR). In addition, PCA can be used for other measurements which give insight to the human vascular properties, for example arterial stiffness. Thus, it is desirable that the measured blood pressure signals be as accurate as possible.

Invasive devices have the disadvantage of being overly disturbing and painful to the patient, whereas signals from non-invasive devices have problems with the fidelity or accuracy of the signal.

SUMMARY

A system and method of digital control for a blood pressure measurement system is disclosed. In one embodiment, a device for continuous blood pressure measurement is disclosed. The device includes a pressure cuff adapted to be placed over an artery in a human finger, the cuff including a PPG system having at least one light source and at least one light detector, a pressure system comprising at least one pump, at least one valve or valve system, and at least one pressure sensor; and a controller for controlling pressure in the cuff by altering the valve or valve system, wherein the one or more light detectors are associated with at least one light-to-frequency conversion (LFC) device.

In another embodiment, a method for continuously measuring blood pressure is disclosed. The method includes placing a photo-plethysmographic (PPG) system over an artery or vein in a human finger, the PPG system producing a PPG signal based on volume of the artery or vein, the PPG system including at least one light source and at least one light detector, utilizing a computing device to alter a pressure inside the cuff by altering a valve or valve system that is connected to a pump and pressure sensor, wherein, based on the measured blood volume of the artery or vein, a frequency signal is produced by a light-to-frequency conversion (LFC) device, and wherein the computing device holds the frequency signal substantially constant by altering the cuff pressure.

In yet another embodiment, a sensor for continuously measuring blood pressure is disclosed. The sensor includes a pressure cuff adapted to be placed over an artery in a human finger, a PPG system inside the cuff having at least one light source and at least one light detector, at least one computing device for receiving and submitting electrical digital signals and power supply signals, one or more air connectors for applying pressure to the cuff, wherein the at least one light detector is configured as a light-to-frequency conversion (LFC) device and, based on measured light, produces a frequency signal to the at least one computing device to the control unit of the sensor.

BRIEF DESCRIPTION OF THE FIGURES

An exemplary embodiment of the present invention is described herein with reference to the drawings, in which.

DETAILED DESCRIPTION

A system and method for enhanced digital control of a continuous non-invasive arterial pressure (CNAP) measurement system is described. The CNAP measurement output signals may then be used to more accurately calculate a variety of parameters for a patient, such as stroke volume (SV), cardiac output (CO), total peripheral resistance (TPR), and arterial stiffness, for example. Such a calculation process may be referred to as Pulse Contour Analysis (PCA).

Figure 1:
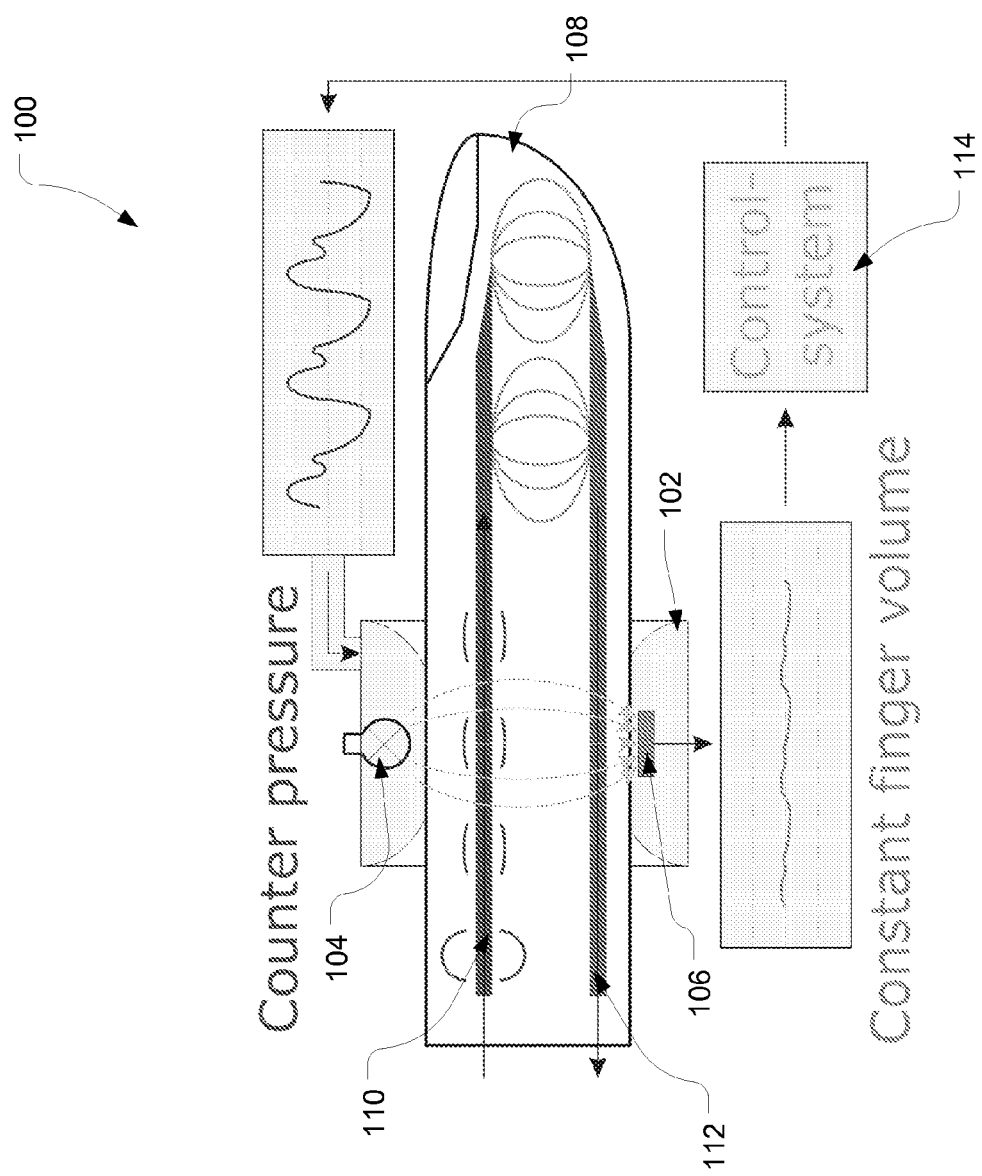
FIG. 1 illustrates a Vascular Unloading Technique (VUT) control system using a photo-plesthysmographic (PPG) system controlling the cuff pressure for measuring blood pressure, in accordance with an embodiment.

FIG. 1 shows a typical "Vascular Unloading Technique" (VUT) system 100 and its control principle, such as that described in copending U.S. patent application Ser. No. 12/915,496, titled "Apparatus and Method for Enhancing and Analyzing Signals from a Continuous Non-Invasive Blood Pressure Device," and filed on an even date herewith, the entire contents of which are incorporated herein by reference. The VUT system 100 includes a "photo-plethysmographic" (PPG) system comprising a finger cuff 102 having one or more light sources 104 and one or more light detectors 106. The PPG-signal is fed into a control system 114 that produces a pressure in the cuff 102.

In operation, a human finger 108 is placed in the finger cuff 102. The finger cuff 102 measures blood volume in an artery 110 of the finger 108. During systole, when blood volume increases in the finger 108, a controller 114 increases the pressure of the finger cuff 102, $p_{cuff}(t)$, until the excess blood volume is squeezed out by pressure of the cuff. On the other hand during diastole, the blood volume in the finger is decreased, and therefore the controller 114 decreases $p_{cuff}(t)$ so the overall blood volume in the artery remains constant. As blood volume and thus $v(t)$ is held constant over time, the pressure difference between cuff pressure $p_{cuff}(t)$ and intra-arterial pressure, $p_{art}(t)$, is zero. Thus, $p_{art}(t)$ is equal to cuff pressure $p_{cuff}(t)$, which can be measured by means of a manometer (pressure measuring instrument), for example. Thus, intra-arterial pressure $p_{art}(t)$ itself is measured indirectly, and a PPG-signal $v(t)$, which reflects the arterial blood volume changes in the measuring area (e.g. the finger) is obtained. As the PPG-signal is kept constant, the counter pressure eliminates the arterial blood volume changes and the diameter of the artery is constant too. So, arterial influx is guaranteed during measurement, whereas return in the vein 112 from the fingertip is slightly reduced.

A PPG system may measure artery volume by emitting light radiation into the artery 110 from one or more light sources 104 and detecting the emitted light that is shone through the finger at one or more light detectors 106. A measurement of the intensity of reflected light relative to the intensity emitted light is indicative of the volume $v(t)$ of the measured artery 110. Any type of light source can be used, including LEDs, laser diodes, or another type of lamp.

For accurate readings, the light source emitter/detector (which may include one or more photodiodes producing photocurrent) is usually as close to the artery as possible. Other electronic components necessary for the measurement, such as signal processing components and/or the power source, are located remotely from the emitter and detector. Typically, these components are electrically connected to the emitter/detector via one or more conductors (wires).

In some methods, the emitter/detector includes at least one photodiode that produces a photocurrent as a result of detecting the light. This photocurrent is fed back into the pressure loop, as described above, to cause an adjustment in the pressure of the cuff, if necessary. Signals of this sort are usually on the order of nano-Amperes. And as such, these signals are especially susceptible to interference (i.e., noise) resulting from neighboring electronic components, such as resistors, high impedance amplifiers, common mode rejection ratio (CMRR) interference, and other interference resulting from conductors. Typically, the photocurrent signals are protected from noise by using electromagnetic shields. However, this shielding technique is not always effective, and, at times, can add cost to the system.

Disclosed herein are different methods. In at least one embodiment of the disclosed methods, the detected light radiation is not converted to a photocurrent; rather, the light energy is converted to an alternating (AC) signal where the frequency of the AC-signal contains the light-information. This frequency (referred to as f(t)) is essentially modulated by the light radiation (referred to as l(t)).

In at least one embodiment, this light-to-frequency conversion is carried out by a device referred to as a light-to-frequency converter. Such a device may carry out what is referred to as a light-to-frequency conversion (LFC). In at least one embodiment, a TSL245 from Texas Instruments can be used for at least such a purpose. The LFC may produce a relatively high frequency when the intensity of light is relatively high. The LFC may produce a relatively low frequency when the intensity of light is relatively low.

An example equation for modeling the LFC is given by Equation 1, where H( ) is the transfer function of the LFC.

$$f(t)=H(l(t)) \qquad (1)$$

The AC-signal (f(t)) from the LFC is thereafter transmitted from the sensor to an electrical control unit, which includes at least a timer unit. The AC-signal is provided to the timer unit as an input. The AC-signal begins a timer kept by the timer unit on a "zero-passing" or an "edge" in one direction (e.g. passing from negative voltage to positive voltage or vice versa). The timer stops when the AC-signal passes zero again or has an edge in the other direction. In this manner, the timer counts and thus, measures, the duration of a half duty cycle. This can be modeled by Equation 2.

$$T/2=1/f(t)=1/H(l(t)) \qquad (2)$$

When the timer stops, the timer unit retains the value of the timer. This timer value is equivalent to the time of the half duty cycle of the LFC-frequency and is inversely proportional to the intensity of light radiation measured by the emitter/detector. When the AC-signal crosses zero, the signal has a high transient (modeling in a best case, a rectangular signal). For at least this reason, the signal is relatively immune to noise.

Further, control systems that take advantage of the present methods can avoid using expensive electronic components, such as instrumentation amplifiers with good CMRR, as well as electromagnetic shields. In at least one embodiment of the present methods, the light signal appears as the timer value and may be used as digital data for any further process.

Figure 2:
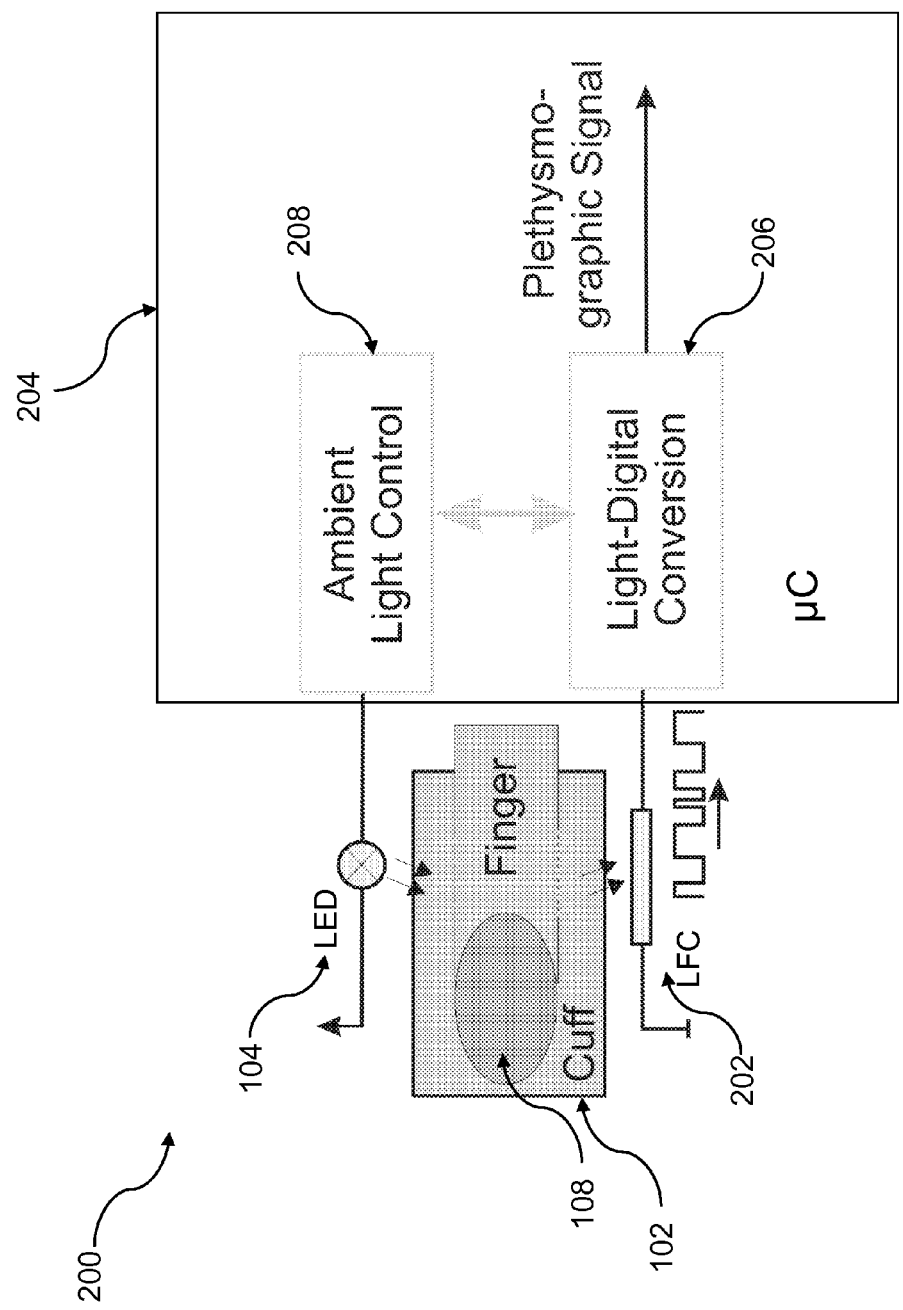
FIG. 2 illustrates a PPG system including light-to-digital conversion and ambient light control, in accordance with an embodiment.

FIG. 2 illustrates an example light control system 200. In at least one embodiment, the light control system produces the digital PPG-signal and eliminates ambient light. The limb 108 (e.g. a finger) is illuminated with light radiation from a light source (e.g. LED 104). The emitted light radiation is transmitted through the limb or reflected at the bone and an LFC device 202 detects the reflected light. Both, LED 104 and LFC device 202 are positioned near the limb 108 and housed inside a cuff 102.

In some embodiments, the LFC device 202 produces (as an output) a square wave signal. This signal contains light information and may be connected to any number of other electrical components or computing devices, such as a microcontroller μC 204. A light-to-digital conversion unit may at least take the form of a microcontroller implemented timer in order to produce a digital time series signal for further processing. An ambient light control unit 208 may control the pulsation of LED 104. During the "off" portion of the LED pulse (referred to as a "blanking interval") ambient light detection can take place.

Figure 3:
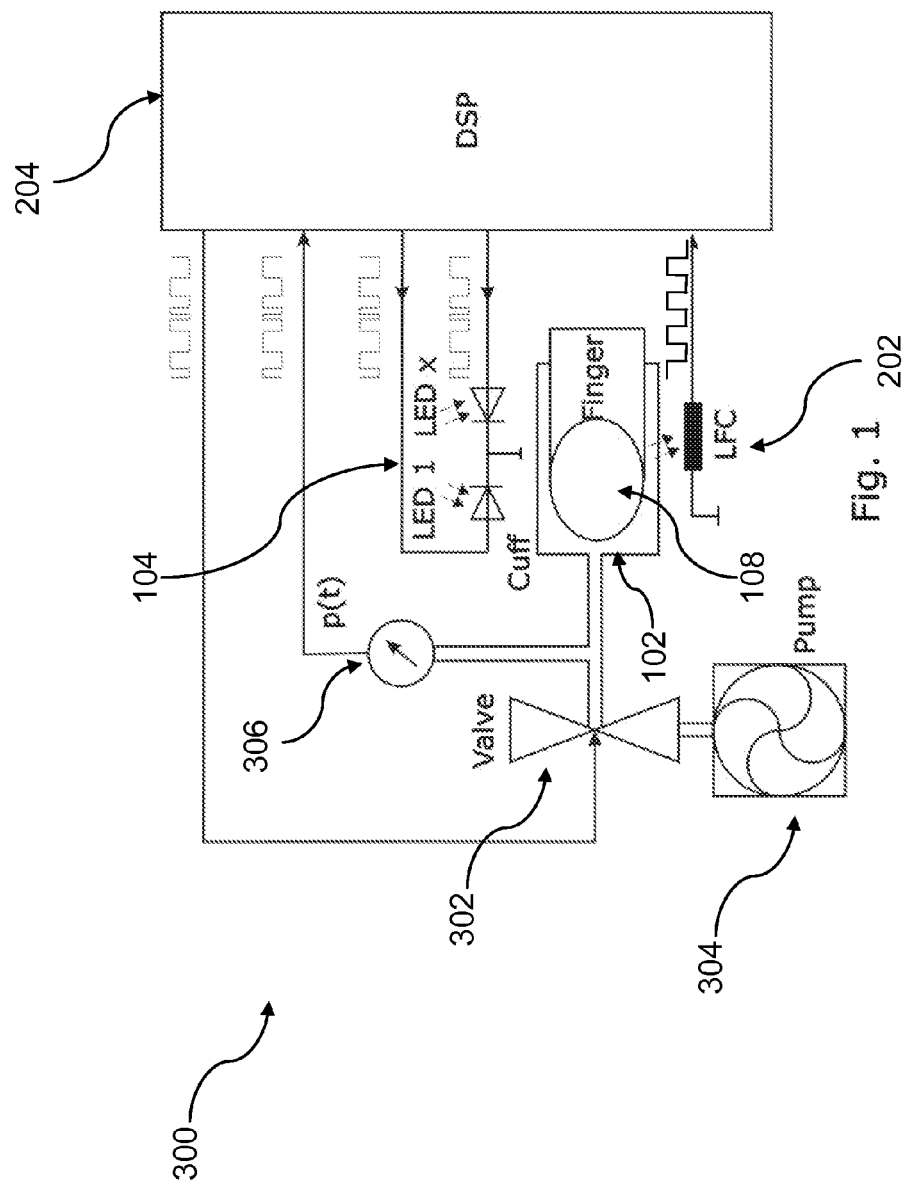
FIG. 3 describes digital control of a VUT system, in accordance with an embodiment.

One advantage of the present systems and methods is shown in FIG. 3. A computing device 204 (e.g., a digital signal processor (DSP)) is receiving signals from the LFC device 202 and from a pressure gauge 306 producing a signal ($p_{cuff}(t)$). Further, the computing device 204 may be submitting at least one control signal to one or more light sources (LED 1 to LED x) and possibly to a valve or a valve system 302. The LED's and valve or valve system 302 may be controlled by duty cycle modulated signals output from the computing device 204 (e.g., pulse width modulated (PWM) signals).

According to VUT methods, the PPG-signal is desired to remain constant. As the PPG-signal (reflected light radiation) is encoded with the LFC-frequency (f(t)), this frequency is similarly desired to remain constant due to the counter pressure $p_{cuff}$.

The computing device 204 (or at least a DSP portion of a computing device) is programmed to carry out one or more digital control loops, which supply the PWM signals to the valve or valve system 302 in order to keep the LFC-frequency, and thus, the duty cycle, constant. This constant value can be obtained utilizing VUT feedback loops.

Figure 4:
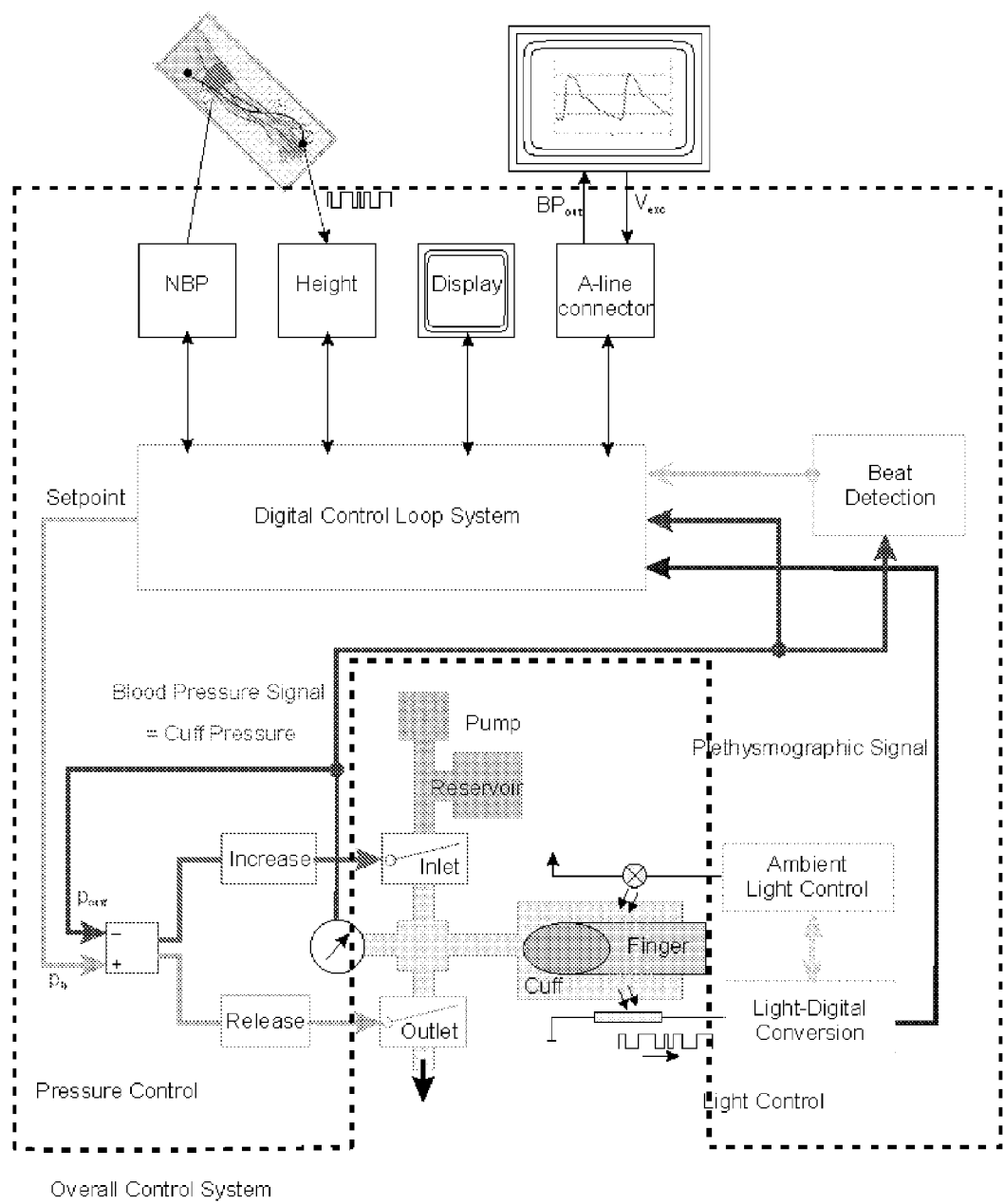
FIG. 4 is a block diagram of a VUT control system, including intermittent NBP height correction and connection to a patent monitor, in accordance with an embodiment.

FIG. 4 illustrates an embodiment of the digital VUT-system. This illustrated system uses a double valve system and two or more control loops. Those skilled in the art will realize that the digital VUT system can operate without the double valve system, possibly with a single control loop. FIG. 4 illustrates the overall principle of at least one embodiment.

The inner loops control the counter pressure inside the finger cuffs using separate inlet and outlet valves for fast reactivity to blood pressure (BP) changes. The inlet valve and the outlet valve each have a control loop and a combined control loop in order to produce a more accurate pressure signal. As can be seen in FIG. 4, a pressure signal from an electronic gauge is fed back to the pressure control unit and compared with the setpoint pressure value calculated from the digital control loop system. If the actual pressure value is lower than desired setpoint pressure value, the increase unit opens the inlet valve to the pump and reservoir site, while the outlet valve is closed. This increases pressure in the device. If the actual value is higher than desired setpoint pressure value, the inlet valve is closed and the release unit opens the outlet valve. This decreases pressure in the device. These loops act quickly by using, for example, piezoelectric valves, which may have a response (e.g., opening/closing) time less than 10 msec. With this fast reacting pressure system, physiologic BP changes can be tracked (followed) with adequate response time. Additionally, there may be no need for precise linearity of the valve system. This allows for easier reproduction and calibration of the system, which results in a less expensive system.

One of the two valves is closed at any time and therefore the pump does not unnecessarily blow air to the outside. Further, there may be no need for a constant filling pressure in the reservoir. Simple and less reliable pumps may be used intermittently and therefore, power consumption and costs may be significantly reduced. These improvements have an impact on the form factor—an important issue especially for devices used in practice settings, such as patient transport, post anesthesia care units (PACUs) and intensive care units (ICUs).

As illustrated by FIG. 4 and FIG. 2, the PPG-system may regulate the effects of surrounding (or ambient) light by an ambient light control method. Thus, a PPG-signal with reduced noise may be encoded into the LFC-frequency that is kept constant by the counter pressure inside the cuff. One or more LEDs and an LFC device of that system can be integrated directly into the cuff.

For regulating pressure according to the VUT methods, a digital control loop system may be used. This system can comprise two or more interlocking control loops. The control loops, as well as all other elements surrounded by the dashed-line in FIG. 4, can be implemented as software on a computing device or DSP. This digitization may simplify associated electrical and mechanical hardware.

In addition, any of the following elements can be integrated with any of the described embodiments: standard NBPs for calibration to upper arm BP-values, height correction systems to correct differences in hydrostatic pressures between finger (sensor level) and heart level, excitation voltages from at least one external monitor device in order to scale the BP-signal to the at least one monitor device, and a display for showing the BP-signal.

The physician is used to blood pressure values that are obtained at heart level. As the finger could be on a different hydrostatic level, the difference between finger and heart level could be corrected with a water filled tube between these two sites. Thus, a height correcting system may be incorporated with at least one embodiment of the described systems and methods in order to eliminate hydrostatic difference of the finger sensor and heart level. Such a height correcting system may consist of a fluid-filled tube, where the density of the fluid corresponds to the density of blood. One end of the tube is placed at heart level, whereas the other end is placed on the finger cuff. A free-floating membrane, which prevents the fluid from escaping, could be attached at the heart end of the tube. A pressure sensor at the finger end connected directly to the fluid measures the hydrostatic pressure difference. The pressure sensor of this height correcting system can be constructed so that a frequency or digital signal at the sensor site is produced and submitted to the overall control system.

The described systems and methods may also produce a scaled version of the BP signal ($p_{cuff}(t)$), while the control system may transform $p_{cuff}(t)$, the single BP values from the calibration device, the input of the height correction, and an excitation voltage coming from a standard patient monitor.

Figure 5:
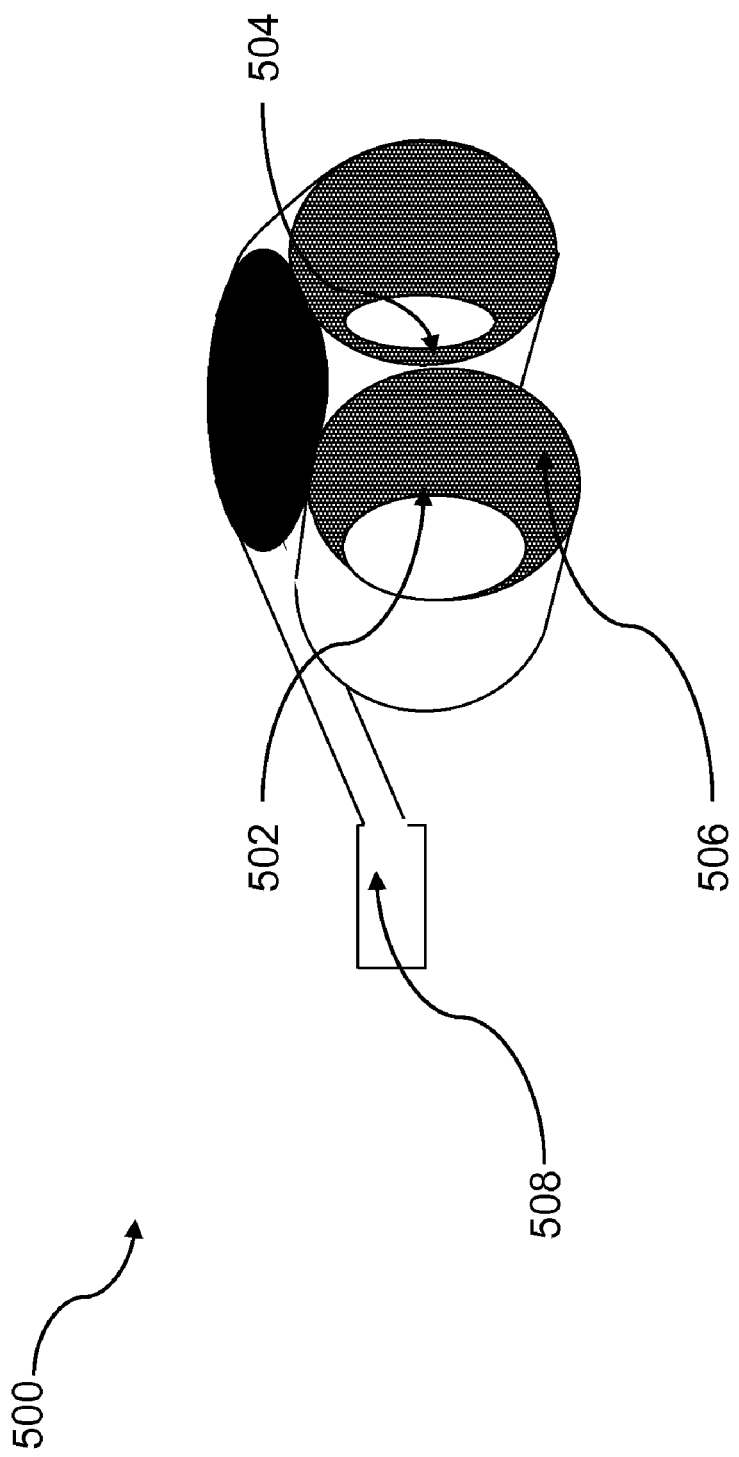
FIG. 5 illustrates an example sensor for measuring blood pressure using a double cuff for measuring blood pressure in one of two fingers alternatively, in accordance with an embodiment.

FIG. 5 illustrates a typical finger sensor 500 embodied as double finger cuff. The sensor switches the measuring finger from time to time in order to avoid pressure marks when having measuring time greater than 1 hour. Each finger sensor consists of a light source (as previously described) in a position 502 (e.g. an LED), light detector configured as a LFC (as previously described) in position 504, and cuff 506. Electrical and air supplies are fed into the sensor over a general connector 508.

Figure 6:
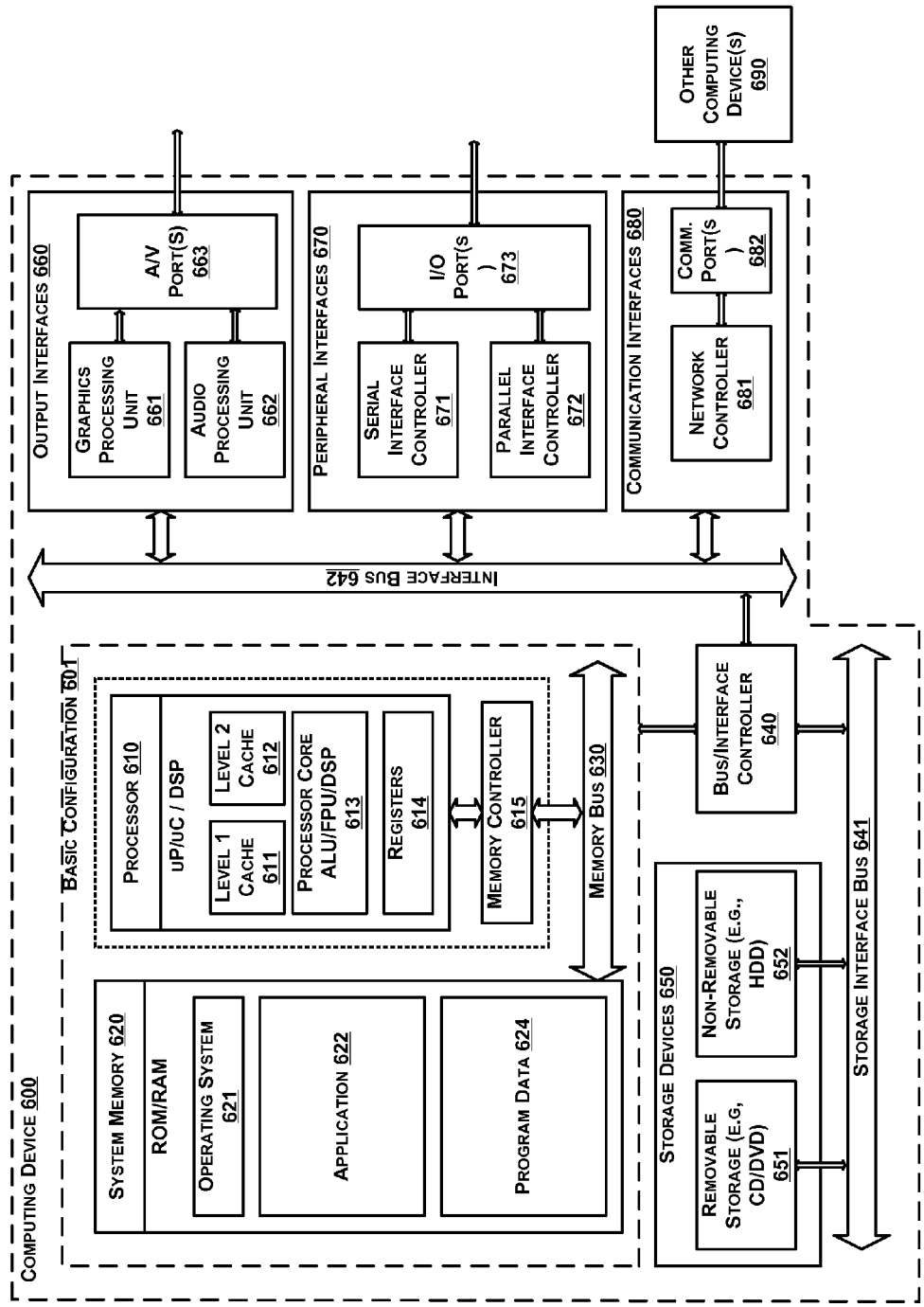
FIG. 6 is a block diagram illustrating an example computing device, in accordance with an embodiment.

FIG. 6 is a block diagram illustrating an example computing device 600 that may be associated with the system and method of the present application and may take the place of at least one computing device already described. The computing device 600 may perform at least one method step of the present application.

In a very basic configuration 601, computing device 600 typically includes one or more processors 610 and system memory 620. A memory bus 630 can be used for communicating between the processor 610 and the system memory 620.

Depending on the desired configuration, processor 610 can be of any type including but not limited to a microprocessor (µP), a microcontroller (µC), a digital signal processor (DSP), or any combination thereof. Processor 610 can include one more levels of caching, such as a level one cache 611 and a level two cache 612, a processor core 613, and registers 614. The processor core 613 can include an arithmetic logic unit (ALU), a floating point unit (FPU), a digital signal processing core (DSP Core), or any combination thereof. A memory controller 615 can also be used with the processor 610, or in some implementations the memory controller 615 can be an internal part of the processor 610.

Depending on the desired configuration, the system memory 620 can be of any type including but not limited to volatile memory (such as RAM), non-volatile memory (such as ROM, flash memory, etc.) or any combination thereof. System memory 620 typically includes an operating system 621, one or more applications 622, and program data 624. For example, an application 622 may be designed to receive certain inputs from the PPG system and base decisions off of those inputs. For instance, the application may be designed to receive inputs from the PPG system, the NBP, and potentially other systems. As an output, the application 622 may carry out any of the methods described herein above and provide a higher fidelity BP signal.

Computing device 600 can have additional features or functionality, and additional interfaces to facilitate communications between the basic configuration 601. For example, a bus/interface controller 640 can be used to facilitate communications between the basic configuration 601 and one or more data storage devices 650 via a storage interface bus 641. The data storage devices 650 can be removable storage devices 651, non-removable storage devices 652, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 620, removable storage 651 and non-removable storage 652 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media can be part of device 600.

Computing device 600 can also include an interface bus 642 for facilitating communication from various interface devices to the basic configuration 601 via the bus/interface controller 640. Example output interfaces 660 include a graphics processing unit 661 and an audio processing unit 662, which can be configured to communicate to various external devices such as a display or speakers via one or more A/V ports 663. Example peripheral interfaces 660 include a serial interface controller 671 or a parallel interface controller 672, which can be configured to communicate with external devices such as input devices (e.g., keyboard, mouse, pen, voice input device, touch input device, etc.) or other peripheral devices (e.g., printer, scanner, etc.) via one or more I/O ports 673. An example communication interface 680 includes a network controller 681, which can be arranged to facilitate communications with one or more other computing devices 690 over a network communication via one or more communication ports 682. The Communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media (or medium) as used herein can include both storage media and communication media.

Computing device 600 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 can also be implemented as a personal computer including both laptop computer and non-laptop computer configurations.

While the invention has been described herein with relation to certain embodiments and applications, those with skill in the art will recognize changes, modifications, alterations, and the like which still come within the spirit of the inventive concept, and such are intended to be within the scope of the invention as expressed in the following claims.

The invention claimed is:

1. A device for continuous blood pressure measurement comprising:
   a pressure cuff adapted to be placed over an artery in a human finger, the cuff including a PPG system having at least one light source and at least one light detector, the at least one light detector being associated with a light-to-frequency (LFC) conversion device that is configured for producing an AC signal based on light intensity measured from the one or more light detectors, wherein a frequency of the AC signal is representative of blood volume in the artery;
   a pressure system comprising:
   at least one pump,
   at least one valve or valve system, and
   at least one pressure sensor; and
   a controller configured for controlling pressure in the cuff by altering the valve or valve system and holding the AC signal substantially constant by altering the pressure in the cuff.

2. The blood pressure measurement device according to claim 1, wherein the controller is a computing device.

3. The blood pressure measurement device according to claim 2, wherein the LFC device is electrically connected to a digital input of the computing device.

4. The blood pressure measurement device according to claim 2, wherein the at least one valve or valve system is controlled via a digital output from the computing device.

5. The blood pressure measurement device according to claim 4, wherein the digital output is a pulse width modulated (PWM) signal.

6. The blood pressure measurement device according to claim 2, wherein the at least one light source and the at least one light detector are controlled via a digital output of the computing device.

7. The blood pressure measurement device according to claim 6, wherein a blanking-interval of the light source is used for ambient light detection.

8. The blood pressure measurement device according to claim 2, wherein the computing device receives information from a calibration device.

9. The blood pressure measurement device according to claim 1, wherein the blood pressure measurement device receives information from a hydrostatic correction system.

10. The blood pressure measurement device according to claim 1, wherein the blood pressure measurement device receives scaling information from at least one other device.

11. The blood pressure measurement device according to claim 10, wherein the blood pressure measurement device calculates a scaled blood pressure curve and transmits the scaled blood pressure curve to the other device.

12. A method for continuously measuring blood pressure comprising:
   placing a photo-plethysmographic (PPG) system over an artery or vein in a human finger, the PPG system producing a PPG signal based on volume of the artery or vein, the PPG system including at least one light source and at least one light detector;
   utilizing a computing device to alter a pressure inside the cuff by altering a valve or valve system that is connected to a pump and pressure sensor,
   wherein, based on the measured blood volume of the artery or vein, a frequency signal is produced by a light-to-frequency conversion (LFC) device, and
   wherein the computing device holds the frequency signal substantially constant by altering the cuff pressure.

13. The method of claim 12, wherein the computing device alters the valve or valve system based on the frequency signal.

14. The method of claim 12, wherein the LFC device produces a frequency output based on light intensity measured from the one or more light detectors.

15. The method of claim 12, further comprising, detecting the ambient light during a blanking-interval of the light source.

16. A sensor for continuously measuring blood pressure comprising:
   a pressure cuff adapted to be placed over an artery in a human finger;
   a PPG system inside the cuff having at least one light source and at least one light detector, the at least one light detector being configured as a light-to-frequency (LFC) conversion device, wherein the LFC device produces an AC frequency signal that is representative of the volume of blood in the artery;
   one or more air connectors for applying pressure to the cuff; and
   at least one computing device comprising:
      a processor; and
      memory storage coupled to the processor having stored thereon instructions, which, when executed by the processor, cause the computing device to carry out functions, the functions comprising causing the one or more air connectors to apply a continuously-changing amount of pressure to the cuff such that the AC frequency signal has a substantially constant frequency, the continuously-changing amount of pressure being representative of a blood pressure measurement for the artery.

17. The sensor of claim 16, wherein causing the one or more air connectors to apply a continuously-changing amount of pressure to the cuff comprises altering a valve or valve system that is connected to a pump and pressure sensor.

18. The sensor of claim 17, wherein altering the valve or valve system that is connected to the pump and pressure sensor comprises using a pulse-width-modulated (PWM) signal to control the valve or valve system, wherein opening and closing of the valve or valve system is a function of a duty cycle of the PWM signal.

* * * * *